United States Patent
Nezu

(10) Patent No.: US 11,147,556 B2
(45) Date of Patent: Oct. 19, 2021

(54) CLOSURE DEVICE

(71) Applicant: NIFCO INC., Yokosuka (JP)

(72) Inventor: Mikio Nezu, Yokosuka (JP)

(73) Assignee: NIFCO INC., Yokosuka (JP)

(*) Notice: Subject to any disclaimer, the term of this patent is extended or adjusted under 35 U.S.C. 154(b) by 0 days.

(21) Appl. No.: 16/279,071

(22) Filed: Feb. 19, 2019

(65) Prior Publication Data

US 2019/0254673 A1     Aug. 22, 2019

(30) Foreign Application Priority Data

Feb. 22, 2018   (JP) .............................. JP2018-029894

(51) Int. Cl.
*A61B 17/08*     (2006.01)

(52) U.S. Cl.
CPC ...... *A61B 17/085* (2013.01); *A61B 2017/081* (2013.01); *A61B 2017/088* (2013.01)

(58) Field of Classification Search
CPC ....... A61F 13/0246; A61M 2025/0266; A61M 2025/0273; A61B 17/08; A61B 17/0466; A61B 17/0487; A61B 17/083; A61B 17/085; A61B 17/06166; A61B 17/064; A61B 17/0401; A61B 2017/00884; A61B 2017/0488; A61B 2017/049; A61B 2017/06157; A61B 2017/081;
(Continued)

(56) References Cited

U.S. PATENT DOCUMENTS 3,214,502 A * 10/1965 Schaar ................ A61F 13/0246

3,971,384 A * 7/1976 Hasson ................ A61B 17/085
606/218
(Continued)

FOREIGN PATENT DOCUMENTS

CN           1712323 A        12/2005
JP         2016-527958         9/2016
(Continued)

OTHER PUBLICATIONS

Japanese Office Action dated Jan. 5, 2021 in Japanese Patent Application No. 2018-029894, 2 pages.
(Continued)

*Primary Examiner* — Melanie R Tyson
*Assistant Examiner* — Uyen N Vo
(74) *Attorney, Agent, or Firm* — Oblon, McClelland, Maier & Neustadt, L.L.P.

(57) ABSTRACT

A closure device 100 that closes a wound on a skin includes a pair of sheet members 41a, 41b that have an axial direction da and a width direction db orthogonal to the axial direction da and face each other with a space 41s provided in the width direction db, and a plurality of closure elements 2a, 2b that are attached to the pair of sheet members 41a, 41b across the space 41s and arranged in the axial direction da. The closure element 2a, 2b respectively include bases 10a, 10b and adjusters 30a, 30b that are arranged on the pair of sheet members 41a, 41b to face each other across the space 41s, and drawstrings 20a, 20b that extend from the bases 10a, 10b and engage with the adjusters 30a, 30b. The pair of sheet members 41a, 41b include a plurality of slits 51, 52 provided in a plurality of areas, each of the plurality of areas being provided between pairs of the closure elements 2a, 2b adjacent to each other.

10 Claims, 5 Drawing Sheets

(58) Field of Classification Search
CPC ...... A61B 2017/088; A61B 2017/0412; A61B 2017/0496; A61B 2017/0618; A61B 2017/00407; A61B 2017/086; A61B 2017/1103; A61B 17/8866
See application file for complete search history.

(56) References Cited

U.S. PATENT DOCUMENTS

| | | | |
|---|---|---|---|
| 2005/0020957 A1* | 1/2005 | Lebner | 602/42 |
| 2016/0206311 A1* | 7/2016 | Belson et al. | A61B 17/085 |
| 2016/0249924 A1* | 9/2016 | Belson | A61B 17/0466 606/216 |

FOREIGN PATENT DOCUMENTS

| WO | WO 2015/012887 A1 | 1/2015 |
|---|---|---|
| WO | WO 2017/200058 A1 | 11/2017 |

OTHER PUBLICATIONS

Office Action issued in corresponding Chinese Patent Application No. 201910132402.X dated Jun. 29, 2021 (with English translation) 16 pages.

* cited by examiner

| | DEGREE OF RESISTANCE TO TEAR AT THE TIME OF APPLICATION (FOLLOWABILITY) | DEGREE OF RESISTANCE TO TEAR AT THE TIME OF PEELING |
|---|---|---|
| EMBODIMENT | EXCELLENT | EXCELLENT |
| FIRST MODIFICATION | EXCELLENT | EXCELLENT |
| SECOND MODIFICATION | GOOD | GOOD |
| THIRD MODIFICATION | MARGINAL | MARGINAL |
| CONVENTIONAL EXAMPLE | POOR | POOR |

CLOSURE DEVICE

CROSS-REFERENCE TO RELATED APPLICATIONS

This application is based upon and claims the benefit of priority from Japanese Patent Application No. 2018-29894, filed on Feb. 22, 2018; the entire contents of which are incorporated herein by reference.

BACKGROUND OF THE INVENTION

Field of the Invention

The present invention relates to a closure device that closes a wound (incisional wound) on a skin.

Background Art

Conventionally, as a closure device that closes a wound on a skin (wound closure), for example, a closure device described in JP 2016-527958A is known. This closure device includes a base that is placed on the skin, a drawstring that is integral with and extends from the base, and an adjuster that is placed on the skin and includes a to-be-engaged section (ratchet mechanism) that is engaged with the drawstring. Projections and depressions are formed on the outer surface of the drawstring and allow the drawstring to move relative to the to-be-engaged section in only one direction (a direction in which the base and the to-be-engaged section come close to each other). Then, in a state where the base and the adjuster are placed on (for example, applied to) the skin across the wound to be closed, the wound is closed via movement of the drawstring relative to the adjuster. As described above, since the drawstring is allowed to move relative to the adjuster in only one direction, once the drawstring is pulled out with respect to the adjuster to close the wound, the wound is kept closed. Such closure devices are connected in parallel with each other in an initial state, and are cut into lengths corresponding to a size of the wound to be closed and then used.

Specifically, in the conventional closure device, a pair of closure elements, each including a base with a drawstring and an adjuster facing each other, constitute one closure unit. A plurality of the closure units arranged in an axial direction of a sheet member constitute the closure device. In a space sandwiched between two closure units adjacent to each other, a single line of perforations extending in a width direction of the sheet member is provided. The presence of these perforations allows the sheet member to be easily cut in accordance with the length of the wound to be closed.

Incidentally, when the wound to be closed is curved, it is desirable that the sheet member be applied to the wound with being curved along the wound. In this case, the conventional closure device is sometimes undesirably separated along the perforations. Therefore, it is difficult to apply the closure device along the wound. Further, in a case where the closure device is applied to the vicinity of a joint such as an elbow or a knee, the closure device is sometimes undesirably separated along the perforations when the joint is bent and stretched. It is of course conceivable to make the perforations less prone to tear, but such a configuration makes the sense of resistance (tightness) caused when the elbow or knee is bent or stretched stronger, which results in poorer comfort. Furthermore, when the closure device is peeled off from the affected part after the wound has healed, the closure device is prone to separation along the perforations, which inhibits rapid peeling.

SUMMARY OF THE INVENTION

The present invention has been made in view of the above problems. That is, an object of the present invention is to provide a closure device that is high in followability to the shape of a wound to be closed and is less prone to separation (less prone to tear) at the time of peeling.

A closure device that closes a wound on a skin according to the present invention includes a pair of sheet members that have an axial direction and a width direction orthogonal to the axial direction and face each other with a space provided in the width direction, and a plurality of closure elements that are attached to the pair of sheet members across the space and arranged in the axial direction, in which, each of the closure elements includes a base and an adjuster that are arranged on the pair of sheet members to face each other across the space, and a drawstring that extends from the base and engages with the adjuster, and the pair of sheet members include a plurality of slits provided in a plurality of areas, each of the plurality of areas being provided between pairs of the closure elements adjacent to each other.

In such a closure device, at least one of the plurality of slits may extend in a direction intersecting the axial direction of the pair of sheet members.

The plurality of slits may include two slits that are adjacent to each other in the axial direction and form a V shape in an area between pairs of the closure elements adjacent to each other.

Alternatively, the plurality of slits may include two slits that are adjacent to each other in the axial direction and extend parallel to each other in an area between pairs of the closure elements adjacent to each other.

The plurality of slits may include at least three slits that are adjacent to each other in the axial direction and extend in a direction intersecting the axial direction in an area between pairs of the closure elements adjacent to each other.

Two of the at least three slits adjacent to each other may be provided at different positions from each other in the width direction of the pair of sheet members.

Further, an apex of the V shape may be directed toward the space.

Alternatively, an opening of the V shape may be directed toward the space.

In the above closure device, each of the closure elements includes a base, a drawstring extending from the base, and an adjuster including a to-be-engaged section that is engaged with the drawstring.

Two of the plurality of closure elements adjacent to each other in the axial direction constitute one closure unit, and in each closure unit, the base of one of the two closure elements and the adjuster of the other of the two closure elements are arranged on one of the pair of sheet members, and the adjuster of the one of the two closure elements and the base of the other of the two closure elements are arranged on the other of the pair of sheet members.

According to the present invention, the closure device that is high in followability to the shape of a wound to be closed and is less prone to separation at the time of peeling can be provided.

DETAILED DESCRIPTION OF THE INVENTION

Embodiment

Hereinafter, an embodiment of the present invention will be described in detail with reference to the accompanying drawings.

Figure 1:
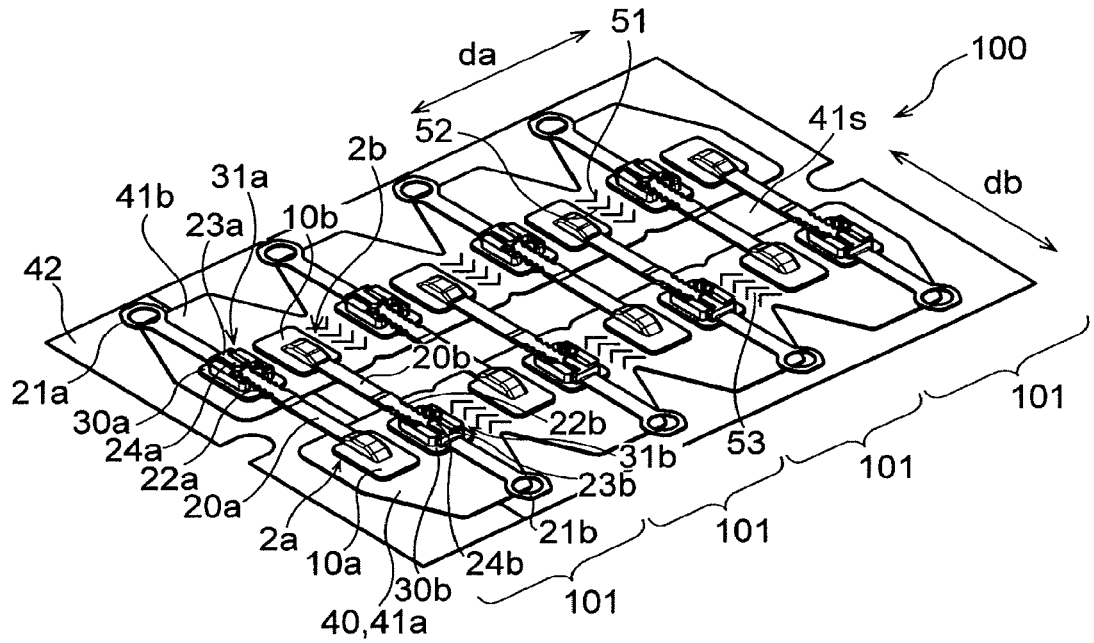
FIG. 1 is a schematic perspective view showing a closure device according to an embodiment of the present invention.
Figure 2:
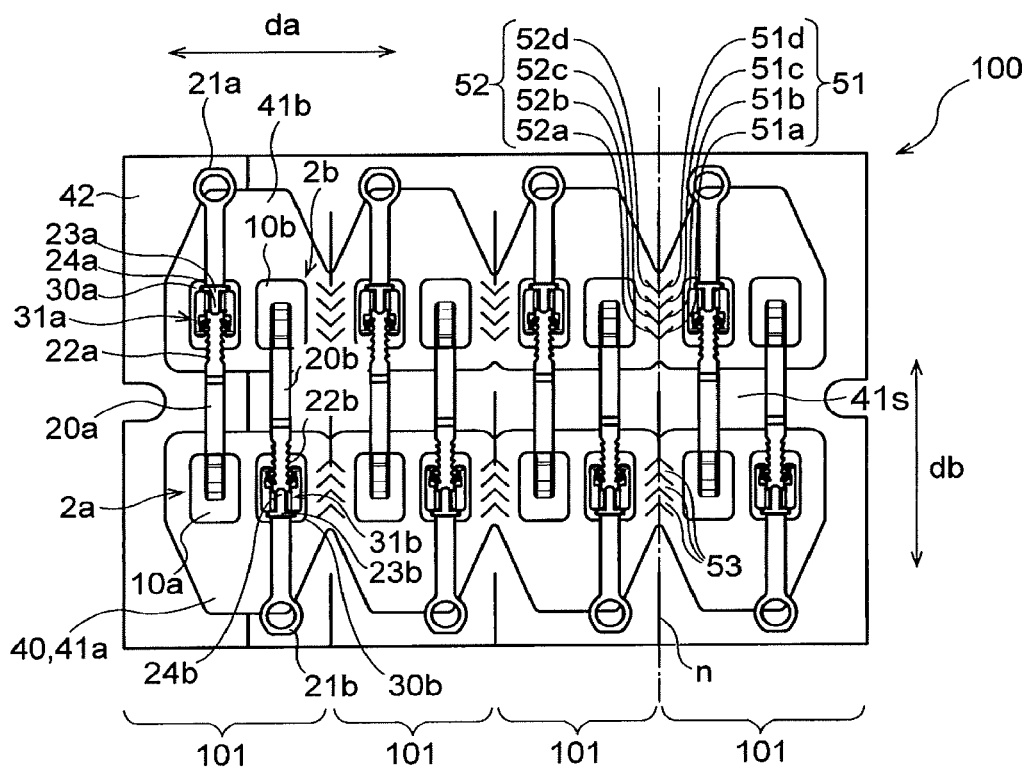
FIG. 2 is a schematic plan view of the closure device of FIG. 1.
Figure 3:
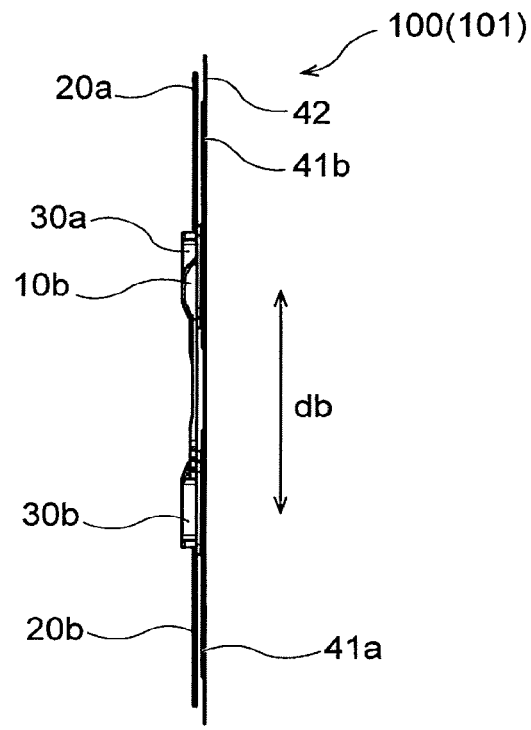
FIG. 3 is a schematic side view of the closure device of FIG. 1.

FIG. 1 is a schematic perspective view showing a closure device 100 according to an embodiment of the present invention. FIG. 2 is a schematic plan view of the closure device 100 of FIG. 1, and FIG. 3 is a schematic side view of the closure device 100 of FIG. 1.

The closure device 100 according to the present embodiment is made of resin and is used for closing a wound (wound closure) such as an incisional wound on a skin formed at the time of surgery. This closure device 100 includes a first closure element 2a and a second closure element 2b, and a first sheet member 41a and a second sheet member 41b on which these two closure elements 2a, 2b are integrally arranged. In the present embodiment, the first sheet member 41a and the second sheet member 41b are surgical tape. As shown in FIGS. 1 and 2, the sheet members 41a, 41b have a common axial direction da. Further, the sheet members 41a, 41b have a width direction db orthogonal to the axial direction da. The first sheet member 41a and the second sheet member 41b faces each other across a space 41s in the width direction db. The first closure element 2a and the second closure element 2b are each extended between the first sheet member 41a and the second sheet member 41b. In other words, the first closure element 2a and the second closure element 2b are each attached to both the first sheet member 41a and the second sheet member 41b d across the space 41s between the first sheet member 41a and the second sheet member 41b. Further, the first closure element 2a and the second closure element 2b are arranged in the axial direction da.

The first closure element 2a includes a first base 10a, a first drawstring 20a that is integrally formed with and extends from the first base 10a, and a first adjuster 30a including a first to-be-engaged section 31a having a shape engageable with the first drawstring 20a. The first base 10a and the first adjuster 30a are arranged on the pair of sheet members 41a, 41b to face each other across the space 41s. The second closure element 2b includes a second base 10b, a second drawstring 20b that is integrally formed with and extends from the second base 10b, and a second adjuster 30b including a second to-be-engaged section 31b having a shape engageable with the second drawstring 20b. The second base 10b and the second adjuster 30b are arranged on the pair of sheet members 41a, 41b to face each other across the space 41s.

An example of the arrangement of the bases 10a, 10b and the adjusters 30a, 30b will be described. In the example shown in FIGS. 1 and 2, the first base 10a of the first closure element 2a and the second adjuster 30b of the second closure element 2b are integrally arranged on the first sheet member 41a, and the adjuster 30a of the first closure element 2a and the base 10b of the second closure element 2b are integrally arranged on the second sheet member 41b. As described above, in the present embodiment, two closure elements 2a, 2b adjacent to each other in the axial direction da constitute one closure unit 101, and a plurality of the closure units 101 are arranged in the axial direction da of the sheet members 41a, 41b As shown in FIGS. 1 and 2, the first closure element 2a and the second closure element 2b of the present embodiment have the same configuration. Therefore, in the following description, when the closure elements 2a, 2b are not clearly distinguished from each other, the closure elements are collectively denoted by a reference numeral 2 (without the symbols a and b). Further, regarding the components of each of the closure elements 2a, 2b, when a component of the first closure element 2a and a component of the second closure element 2b are distinguished from each other, the symbol "a" (corresponding to the first closure element) or the symbol "b" (corresponding to the second closure element) is appended to the reference numeral, but when the components are not clearly distinguished from each other, neither of the symbols is appended, and only the numeral is shown.

Figure 4:
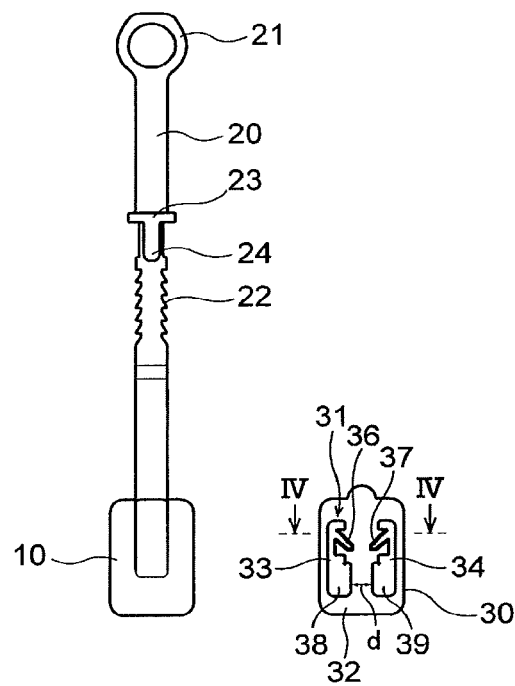
FIG. 4 is a schematic top view showing components, of two closure elements of FIG. 1, arranged on a first sheet member.
Figure 5:
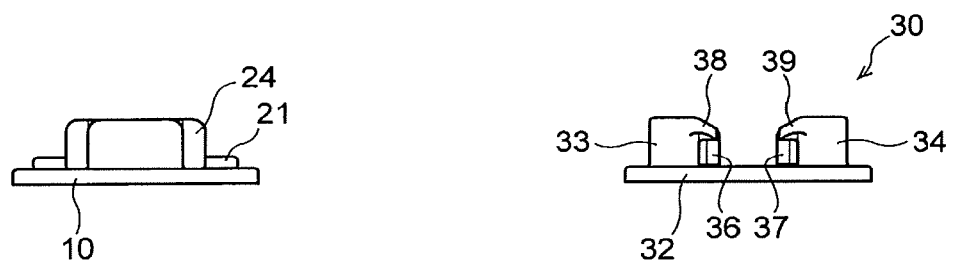
FIG. 5 is a schematic front view of the components of FIG. 4.

FIG. 4 is a schematic top view showing components of the closure elements 2a, 2b arranged on the first sheet member 41a. FIG. 5 is a schematic front view of the components of FIG. 4, and FIG. 6 is a cross-sectional view taken along line VI-VI of FIG. 4.

Figure 6:
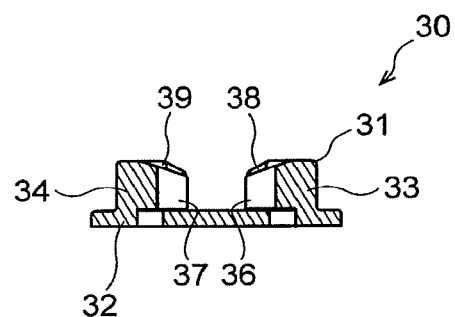
FIG. 6 is a cross-sectional view taken along line VI-VI of FIG. 4.

As shown in FIGS. 4 to 6, the base 10 has a substantially rectangular shape with four corners rounded when viewed from the top, and an adhesive section (not shown) for bonding the base 10 to the sheet member 41 is provided on a skin-side surface of the base 10 (a surface on a back side in FIG. 4 and a lower surface in FIGS. 5 and 6).

The drawstring 20 integrally formed with the base 10 extends from the base 10 and has a tab 21 formed at a distal end thereof. The drawstring 20 includes a plurality of engaging sections 22 formed on both sides thereof, the engaging sections 22 protruding in a direction forming an obtuse angle with respect to a pulling direction of the drawstring 20. These engaging sections 22 engage with a to-be-engaged section 31 (to be described later) to regulate a position of the adjuster 30 relative to the base 10. Further, the drawstring 20 includes a stopper 23 protruding in a direction orthogonal to the pulling direction, and a raised section 24 formed on an upper surface of the drawstring 20 and having a predetermined length toward the base 10. As shown in FIG. 4, the stopper 23 and the raised section 24 are integrally formed with each other.

Next, the adjuster 30 includes a flat plate 32 having a substantially rectangular shape that is substantially identical in dimension to the base 10. An adhesive section (not shown) is provided on a skin-side surface of the flat plate 32 (a surface on the back side in FIG. 4 and a lower surface in FIGS. 5 and 6) in the same manner as the base 10. The to-be-engaged section 31 is provided on an upper surface of the flat plate 32. As shown in FIG. 4, this to-be-engaged section 31 includes a pair of walls 33, 34 between which the drawstring 20 is sandwiched. The pair of walls 33, 34 have engaging claws 36, 37 formed on respective surfaces thereof that faces each other, the engaging claws 36, 37 being engageable with the engaging sections 22 of the drawstring 20.

On respective upper portions (portions on a front side in FIG. 4) of the pair of walls 33, 34, ceiling walls 38, 39 that cover the drawstring 20 engaging with the adjuster 30 are provided at positions advanced in the pulling direction of the drawstring 20 (lower positions in FIG. 4). The ceiling walls 38, 39 and the pair of walls 33, 34 are arranged such that the drawstring 20 can pass through a space surrounded by the walls. A distance d between the ceiling walls 38, 39 is slightly greater than the width of the raised section 24 of the drawstring 20, but is less than the width of the stopper 23. Such a configuration brings the ceiling walls 38, 39 into contact with the stopper 23 of the drawstring 20, which causes the ceiling walls 38, 39 to serve as a locking section that prevents the drawstring 20 from undesirably coming off from the adjuster 30.

Such a closure device 100 is covered with a release paper 42 that prevents dirt or the like from adhering to an adhesive layer provided on the back surface of the sheet member 41 (surgical tape).

Returning to FIGS. 1 and 2, on the pair of sheet members 41a, 41b of the present embodiment, a plurality of slit rows 51, 52 are provided in at least one of areas between pairs of the closure elements 2a, 2b adjacent to each other when viewed along the axial direction da. More specifically, pluralities of slit rows 51, 52 are provided, when viewed along the axial direction da, in a plurality of areas between two closure units 101 adjacent to each other on each of the sheet members 41a, 41b. "Pluralities of slit rows 51, 52 are provided when viewed along the axial direction da" means that the plurality of slit rows 51 and the plurality of slit rows 52 are each provided at a plurality of positions in the axial direction da. In the example shown in FIGS. 1 and 2, the pluralities of slit rows 51, 52 are provided in all the areas between each two closure units 101 adjacent to each other on each of the sheet members 41a, 41b when viewed along the axial direction da. The pluralities of slit rows 51, 52 respectively include a plurality of slits 51a to 51d and a plurality of slits 52a to 52d aligned along the width direction db. Note that, in another embodiment, the slit rows 51, 52 may be each composed of a single slit.

Of the pluralities of slits 51a to 51d and 52a to 52d of the present embodiment, as shown in FIG. 2, each two slits with reference numerals to which the same letter of alphabet is appended are formed with respective proximal ends positioned at an apex of a V shape. Further, as shown in FIG. 2, the slits 51a to 51d in each slit row 51 are parallel to each other, and the slits 52a to 52d in each slit row 52 are also parallel to each other. In the present embodiment, an apex of the V shape formed by each pair of the slits 51a to 51d and 52a to 52d is directed toward a wound to be closed, that is, toward the space 41s between the pair of sheet members 41a, 41b.

The presence of such V-shaped slits causes two closure units 101 adjacent to each other are connected with each other via a plurality of V-shaped bending sections 53. These bending sections 53 consist of portions of the sheet members 41a, 41b defined by each pair of the slits 51a to 51d and 52a to 52d arranged in a V shape. As shown in FIGS. 1 and 2, in the closure device 100 according to the present embodiment, such bending sections 53 are provided in all the areas between each two closure units 101 adjacent to each other.

Next, an effect exhibited by the closure device 100 of the present embodiment will be described.

First, the closure device 100 is cut, as necessary, into dimensions (lengths in the axial direction da) necessary and sufficient for closing the wound to be closed. This cut may be made between two adjacent closure units 101, for example.

In an initial state of the closure device 100, the stopper 23 of the drawstring 20 is in contact with respective edges of the ceiling walls 38, 39 of the adjuster 30, and the raised section 24 is positioned between the ceiling walls 38, 39.

Such a configuration prevents the drawstring 20 from moving in a direction opposite to the pulling direction with respect to the adjuster 30, which prevents the drawstring 20 from coming off the adjuster 30.

Next, the release paper 42 covering a back of the sheet member 41 is peeled off, which exposes the adhesive section formed on the back of the sheet member 41. Then, the closure device 100 is applied onto a skin such that the first sheet member 41a and the second sheet member 41b are positioned across the wound to be closed. Prior to this application, in order to enhance adhesion of the adhesive section of the sheet member 41 to the skin, it is preferable that a surface of the skin being subject to the application is cleaned and dried in advance.

Further, when the wound is curved, in order to more effectively close the wound, it is preferable that the first sheet member 41a and the second sheet member 41b are curved along the wound and then applied onto the skin. As described above, the first sheet member 41a and the second sheet member 41b of the closure device 100 according to the present embodiment include the plurality of V-shaped bending sections 53 in areas between each two closure units 101 adjacent to each other. Therefore, flexural deformation of the bending sections 53 causes the closure device 100 to be placed along the curved shape of the wound while causing each of the closure units 101 to follow the curved shape of the wound. At this time, since the bending sections 53 has a V shape, it can withstand relatively large flexural deformation. This prevents the closure device 100, when the closure device 100 is placed along the shape of the wound, from being undesirably broken at the bending sections 53.

Then, a first tab 21a of the first drawstring 20a of the first closure element 2a and the second tab 21b of the second drawstring 20b of the second closure element 2b are simultaneously pulled. This moves each drawstring 20 in the pulling direction with respect to a corresponding to-be-engaged section 31, which causes a substantially uniform force to act on living tissue around the wound. This pulling operation causes the base 10 and the adjuster 30 to come close to each other. That is, the living tissue around the wound is moved by the first and second sheet members 41a, 41b to close the wound. This pulling operation is performed so that a force necessary and sufficient for closing the wound acts on the living tissue around the wound.

When the drawstring 20 moves in the pulling direction with respect to the to-be-engaged section 31, protrusions of the engaging sections 22 of the drawstring 20 pass through between the engaging claws 36, 37 while flexural-deforming the engaging claws 36, 37 in the pulling direction. On the other hand, moving the engaging sections 22 in a direction opposite to the pulling direction beyond the engaging claws 36, 37 causes the protrusions to interfere with the engaging claws 36, 37, which restricts the movement of the drawstring 20. As described above, since the engaging claws 36, 37 are curved in the pulling direction, curvature deformation of the engaging claws 36, 37 in the pulling direction is relatively easy, while curvature deformation in a direction opposite to the pulling direction is practically impossible. This configuration allows the drawstring 20 to move only in the pulling direction.

The pulling operation of such a tab 21 (drawstring 20) is performed throughout the closure device 100. As a result, the wound to be closed is completely closed. Then, a portion of the drawstring 20 that has been pulled out beyond the engaging claws 36, 37 by the pulling operation is cut off by a suitable cutting tool. As a result, closing of the wound by the closure device 100 is completed.

When the living tissue around the wound is moved via bending and stretching of a joint with the wound closed, such a closure device 100 exhibits good followability to the living tissue due to the presence of the bending sections 53.

Maintaining the state where the wound is closed for a certain period of time causes portions of the living tissue separated by the wound to be joined to each other, thereby causing the wound to heal. Thereafter, the sheet member 41 is removed from the skin. At the time of this removal, the bending sections 53 are flexural-deformed in moderation, which prevents the closure device 100 from being undesirably separated between two closure units 101 adjacent to each other.

According to the present embodiment as described above, the pluralities of slit rows 51, 52 are provided in areas sandwiched between two closure units 101 adjacent to each other on the sheet member 41 when viewed along the axial direction da. This makes it possible to provide the closure device 100 that is high in followability to the shape of the wound to be closed and is less prone to separation at the time of peeling.

Note that a plurality of slits may be provided between two closure elements 2a, 2b of the closure unit 101 when viewed along the axial direction da. In this case as well, the same effect as the effect of the present embodiment can be exhibited.

Further, each pair of the slits 51a to 51d and 52a to 52d in the pluralities of slit rows 51, 52 extend in a direction intersecting the axial direction da of the pair of sheet members 41a, 41b. More specifically, of the slits 51a to 51d and 52a to 52d positioned in areas between two closure units 101 adjacent to each other, two slits adjacent to each other in the axial direction da are formed into a V shape. This forms the flexible bending sections 53 between the two closure units 101 adjacent to each other, which makes it possible to further enhance the followability to the shape of the wound to be closed.

Further, the to-be-engaged section 31 includes the pair of walls 33, 34 between which the drawstring 20 is sandwiched, and the pair of walls 33, 34 include the engaging claws 36, 37 formed on surfaces thereof that face each other, the engaging claws 36, 37 being engageable with the engaging sections 22 of the drawstring 20. This configuration allows the engagement position between the drawstring 20 and the adjuster 30 to be easily adjusted via pulling out of the drawstring 20 from between the pair of walls 33, 34.

Furthermore, the drawstring 20 includes the stopper 23 that protrudes in a direction orthogonal to the pulling direction of the drawstring 20, and the ceiling walls 38, 39 of the adjuster 30 come into contact with the stopper 23 to prevent the drawstring 20 from coming off from the adjuster 30. This configuration effectively avoids a situation where the drawstring 20 falls off the adjuster 30 and then the workability of the wound closure is undesirably impaired.

It is also possible to provide the closure device 100 that can easily close the wound evenly due to the configuration where the respective pulling directions of the drawstrings 20 for closing two closure elements 2a, 2b adjacent to each other are opposite to each other.

In the above embodiment, each pair of the slits 51a to 51d and 52a to 52d are formed, in the sheet member 41, into a V shape whose apex is directed toward the wound, that is, toward the space 41s between the pair of sheet members 41a, 41b, but the present invention is not limited to such a mode. Examples of the slit pattern that can be adopted into modifications of the closure device 100 according to the above-described embodiment will be given below. Note that the configuration other than the slit pattern is the same as the configuration of the above-described embodiment; thus, only the slit pattern will be described in the following description.

(First Modification)

Figure 7:
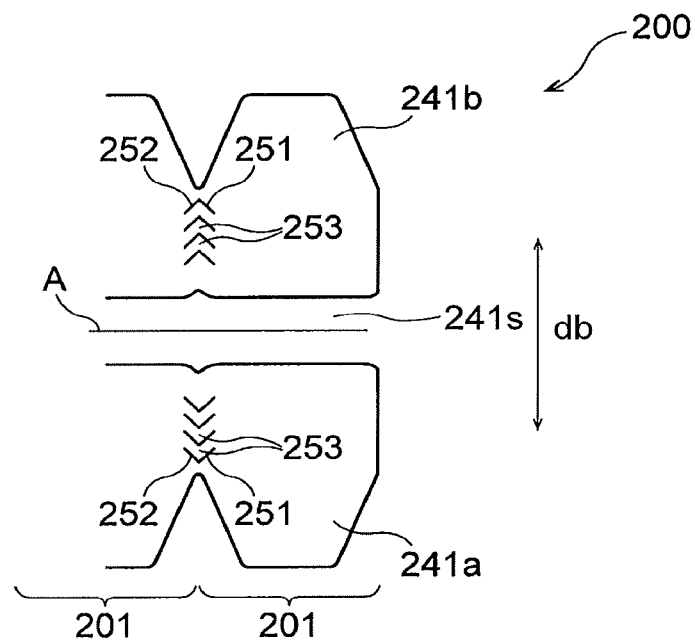
FIG. 7 is a schematic plan view showing a slit pattern of a closure device according to a first modification of FIG. 1.

FIG. 7 is a schematic plan view showing slit rows 251, 252 provided in a closure device 200 according to a first modification. For the sake of clarity, in FIG. 7, only sheet members 241 and the slit rows 251, 252 are shown. Such an illustration is also applied to FIGS. 8 and 9 to be described later.

As shown in FIG. 7, as in the closure device 200 according to the present modification, a plurality of the slit rows 251, 252 positioned in areas between two closure units adjacent to each other are formed, in the sheet members 241, into a V shape. However, an orientation of the V shape is opposite to the orientation of the V shape in the closure device 100 described above. That is, each pair of slits included in the slit rows 251, 252 shown in FIG. 7 are formed in the pair of sheet members 241a, 241b such that the V shape is directed toward a wound A to be closed, that is, an opening of the V shape is directed toward a space 241s between the pair of sheet members 241a, 241b. Therefore, in the present modification, bending sections 253 whose orientation is opposite to the orientation in the above-described embodiment are formed between two closure units 201 adjacent to each other (not shown).

(Second Modification)

Figure 8:
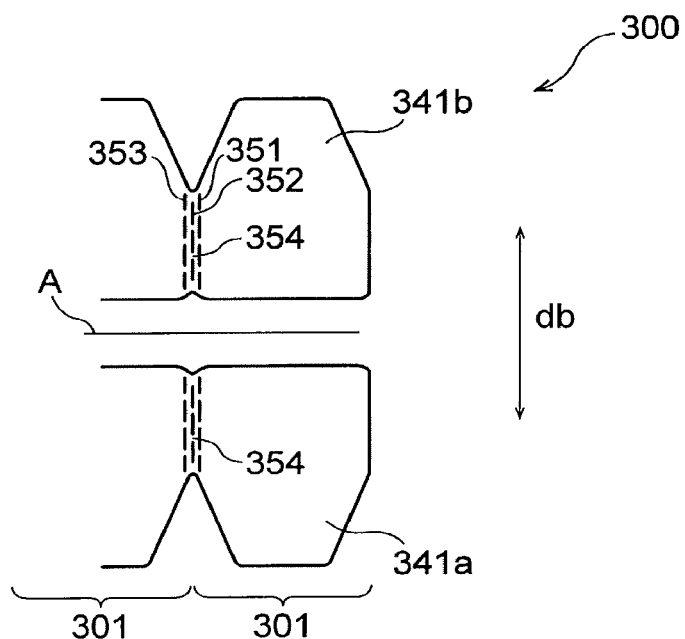
FIG. 8 is a schematic plan view showing a slit pattern of a closure device according to a second modification of FIG. 1.

Next, FIG. 8 is a schematic plan view showing slit rows 351 to 353 provided in a closure device 300 according to a second modification.

The present modification is different from the above-described embodiment and first modification in that a plurality of slit rows, for example, three slit rows 351 to 353, positioned in an area between two closure units adjacent to each other are formed in parallel with the width direction db of each sheet member 341a, 341b. Each of the slit rows 351 to 353 includes a plurality of slits (corresponding to solid black lines in FIG. 8) formed in the width direction of the sheet member 341. The plurality of slits have the same length in the width direction db of the sheet members 341a, 341b except for both end slits.

Further, two slit rows 351 and 352 adjacent to each other have different phases in the width direction db of the sheet member 341, and two slit rows 352 and 353 adjacent to each other also have different phases in the width direction of the sheet member 341. In the present modification, the slit rows 351 and 352, and the slit rows 352 and 353 are out of phase with each other by a half wavelength. Such a configuration forms, between two closure units 301 adjacent to each other, a flexible section 354 that can extend into a so-called mesh decoration shape. When the wound is closed using the closure device 300 according to the present modification, this flexible section 354 freely extends to cause the closure device 300 to be applied onto a skin while satisfactorily following the shape of the wound.

(Third Modification)

Figures 9, 10:
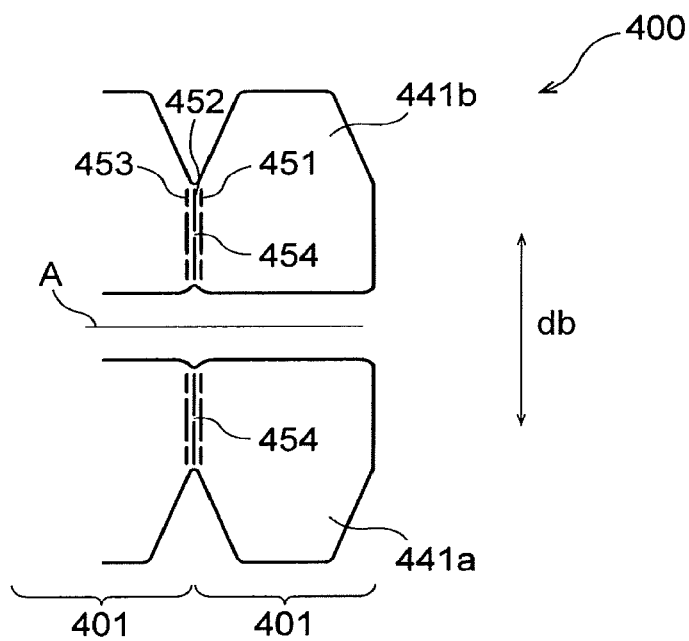
FIG. 9 is a schematic plan view showing a slit pattern of a closure device according to a third modification of FIG. 1.
FIG. 10 is a table showing a list of respective evaluation results of the closure devices on followability at the time of application and resistance to tear at the time of peeling.

Next, FIG. 9 is a schematic plan view showing slit rows 451 to 453 provided in a closure device 400 according to a third modification. Each slit in these slit rows 451 to 453 has a length in the width direction db about twice as long as each slit in the closure device 300 shown in FIG. 8. Therefore, a flexible section 454 formed in the closure device 400 is coarser than the flexible section 354 of the above-described second modification. The other configuration is the same as the configuration in the second modification.

Results of evaluations performed on resistance to tear at the time of application and peeling of each of the closure devices 100 to 400 are listed in a table shown in FIG. 10. Terms "EXCELLENT", "GOOD", "MARGINAL", and "POOR" in the table each indicate a degree of resistance to tear. "EXCELLENT" means that the closure device did not tear with sufficient margin, "GOOD" means that the closure device did not tear but with margin less than the margin of "EXCELLENT", "MARGINAL" means that there was a slit row that partially tears, and "POOR" means that the closure device easily tore. Note that a conventional product corresponds to a closure device in which a single line of perforations is formed in the width direction db between two closure units adjacent to each other.

As can be understood from the table of FIG. 10, it has been shown that any of the closure devices 100 to 400 has the ability to follow the shape of the wound to be closed and is less prone to separation at the time of peeling as compared with the conventional closure device. In particular, in the closure devices 100, 200 having the slits formed into a V shape between two closure units adjacent to each other, the followability at the time of application and the resistance to tear at the time of peeling are excellent.

Note that, in any of the closure devices, it is preferable that no slit is formed on the edges in the width direction of the pair of sheet members. Such a configuration prevents stress from concentrating at the edges and allows the closure device to be less prone to tear at the time of application and/or peeling.

The invention claimed is:

1. A closure device that closes a wound on a skin, comprising:
    a first sheet member and a second sheet member that have an axial direction and a width direction orthogonal to the axial direction and face each other with a space provided in the width direction; and
    a plurality of closure elements that are attached to the first sheet member and the second sheet member across the space and arranged in the axial direction,
    wherein each of the closure elements includes a base and an adjuster that are arranged on the first sheet member and the second sheet member to face each other across the space, and a drawstring that extends from the base and engages with the adjuster,
    the first sheet member includes at least one slit area between the two drawstrings adjacent to each other in the axial direction, the slit area including at least one first slit and at least one second slit adjacent to the first slit in the axial direction, and
    the second sheet member includes at least one slit area between the two drawstrings adjacent to each other in the axial direction, the slit area including at least one first slit and at least one second slit adjacent to the first slit in the axial direction.

2. The closure device according to claim 1, wherein the first slit or the second slit extends in a direction intersecting the axial direction.

3. The closure device according to claim 2, wherein the first slit and the second slit form a V shape.

4. The closure device according to claim 2, wherein the first slit and the second slit extend parallel to each other.

5. The closure device according to claim 2, wherein each of the slit areas includes at least one third slit adjacent to the first slit or the second slit, the first slit, the second slit and the third slit extending in a direction intersecting the axial direction.

6. The closure device according to claim 5, wherein two of the first slit, the second slit and the third slit are provided at different positions from each other in the width direction.

7. The closure device according to claim 3, wherein an apex of the V shape is directed toward the space.

8. The closure device according to claim 3, wherein an opening of the V shape is directed toward the space.

9. The closure device according to claim 1, wherein
    two of the closure elements adjacent to each other in the axial direction constitute one closure unit, and
    in each closure unit,
    the base of one of the two closure elements and the adjuster of the other of the two closure elements are arranged on one of the first sheet member and the second sheet member, and
    the adjuster of the one of the two closure elements and the base of the other of the two closure elements are arranged on the other of the first sheet member and the second sheet member.

10. The closure device according to claim 1, wherein
    each of the slit areas comprises a first row including at least one first slit aligned along the width direction and a second row including at least one second slit aligned along the width direction.

* * * * *